US00PP11947P2

(12) United States Plant Patent
Booman

(10) Patent No.: US PP11,947 P2
(45) Date of Patent: Jun. 19, 2001

(54) BEGONIA PLANT NAMED 'BOSTON CHERRIES 'N CHOCOLATE'

(76) Inventor: James Lawrence Booman, 2302 Bautista Ave., Vista, CA (US) 92084

( * ) Notice: Subject to any disclaimer, the term of this patent is extended or adjusted under 35 U.S.C. 154(b) by 0 days.

(21) Appl. No.: 09/375,777

(22) Filed: Aug. 17, 1999

(51) Int. Cl.[7] ..... A01H 5/00
(52) U.S. Cl. ..... Plt./343

(58) Field of Search ..... Plt./343

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Rex Begonia plant named 'Boston Cherries 'n Chocolate', characterized by its uniform growth habit; moderate plant vigor; no requirement for winter dormancy; and interesting and attractive leaf coloration and pattern.

1 Drawing Sheet

BACKGROUND OF THE INVENTION

The present invention relates to a new and distinct cultivar of Begonia plant, botanically known as *Begonia rex* hybrid, commercially known as Rex Begonia, and hereinafter referred to by the name 'Boston Cherries 'n Chocolate'.

The new Rex Begonia was discovered and selected by the Inventor in a controlled environment in Vista, Calif., in 1995, within a large group of seedling progeny from multiple crossings of unidentified selections of *Begonia rex* hybrids.

The selection of this plant was based on its uniform growth habit, moderate plant vigor, salt tolerance and attractive foliage coloration and pattern.

Asexual reproduction of the new Rex Begonia by leaf cuttings taken in a controlled environment in Vista, Calif., has shown that the unique features of this new Rex Begonia are stable and reproduced true to type in successive generations.

SUMMARY OF THE INVENTION

The cultivar 'Boston Cherries 'n Chocolate' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Boston Cherries 'n Chocolate'. These characteristics in combination distinguish 'Boston Cherries 'n Chocolate' as a new and distinct Rex Begonia:

1. Uniform growth habit.
2. Moderate plant vigor.
3. Does not require winter dormancy.
4. Interesting and attractive leaf coloration and pattern.

In side-by-side comparisons conducted by the Inventor in Vista, Calif., plants of the new Rex Begonia differ from plants of the nonpatented cultivar 'Merry Christmas Corkscrew' in the following characteristics:

1. Plants of the new Rex Begonia have flatter leaves than plants of the cultivar 'Merry Christmas Corkscrew)'.

2. Leaves of plants of the new Rex Begonia and the cultivar 'Merry Christmas Corkscrew' differ in coloration and pattern.
3. Leaves of plants of the new Rex Begonia do not have a "corkscrew" formation whereas leaves of plants of the cultivar 'Merry Christmas Corkscrew' have a "corkscrew" formation.
4. Plants of the new Rex Begonia do not require a winter dormancy period whereas plants of the cultivar 'Merry Christmas Corkscrew' do require a winter dormancy period.

In side-by-side comparisons conducted by the Inventor in Vista, Calif., plants of the new Rex Begonia differ from plants of the nonpatented cultivar 'Lillium'in the following characteristics:

1. Plants of the new Rex Begonia are more compact than plants of the cultivar 'Lillium'.
2. Plants of the new Rex Begonia have flatter leaves than plants of the cultivar 'Lillium'.
3. Leaves of plants of the new Rex Begonia and the cultivar 'Lillium' differ in coloration and pattern.
4. Plants of the new Rex Begonia do not require a winter dormancy period whereas plants of the cultivar 'Lillium' do require a winter dormancy period.

BRIEF DESCRIPTION OF THE PHOTOGRAPH

The accompanying colored photograph illustrates the overall appearance of the new Rex Begonia, showing the colors as true as it is reasonably possible to obtain in colored reproductions of this type. The photograph comprises a top perspective view of a typical plant of 'Boston Cherries 'n Chocolate'. Foliage colors in the photograph may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown during the spring in Vista, Calif., under conditions which approximate commercial practice. Plants used for this description were grown in 15-cm containers for about 3 months.

Botanical classification: *Begonia rex* hybrid cultivar 'Boston Cherries 'n Chocolate'.

Commercial classification: Rex Begonia.

Parentage: Chance seedling of multiple crossings of unidentified selections of *Begonia rex* hybrids.

Propagation:

*Type.*—Leaf cuttings.

*Time to initiate roots, summer.*—About 56 days at 21° C.

*Time to initiate roots, winter.*—About 56 days at 21° C.

*Time to develop roots, summer.*—About 84 days at 21° C.

*Time to develop roots, winter.*—About 98 days at 21° C.

*Rooting habit.*—Fine, fibrous and well-branched.

Plant description:

*Plant form.*—Rosette; compact; dense and outwardly arching potted plant; freely basal branching with good leaf petiole strength.

*Vigor.*—Moderate.

*Plant height, soil surface to top of leaf canopy.*—About 20.5 cm.

*Plant width.*—About 48 cm.

*Leaves.*—Arrangement: Simple. Length: Petiole to apex: About 10.5 cm. Base to apex: About 15.1 cm. Width: About 11.7 cm. Shape: Oblique, ovoid. Apex: Acute. Base: Asymmetrically cordate; somewhat overlapping. Margin: Pectinate; irregularly undulate. Texture: Leathery, rugose; pubescence on lower surface veins. Color: Young foliage, upper surface: Margin: Dark brown, 200A. Midvein areas: 200A merging with 200C. Blade: Many spots of merged 186C to 187B; intermarginal flushes of 141B. Young foliage, lower surface: Margin: 187A. Midvein and following lateral veins: 187A; shading/bleeding to 185D. Background: 140B to 140C. Mature, fully expanded, foliage, upper surface: Margin: Dark brown, darker than 200A, close to 202A. Central venal areas: 200A or close to 202A. Blade: Darker than 200A, fading to 200A. Velvety with blistered spots of 185A to 187B. Flush of 143A. Veins: 187A to 200B. Mature, fully expanded, foliage, lower surface: Margin: 187A. Central venal area: 187A. Blade: Splotches of 171B and 194B. Veins: 187A; reticulate.

*Petioles.*—Length: About 13.3 cm. Diameter: About 6 mm. Shape: Canaliculate. Texture: Pubescent. Color: 178A to 178B with 145B to 146C at leaf base.

*Stipules.*—Length: About 17 mm. Diameter at base: About 8 mm. Shape: Deltoid. Color: Close to 184B to 184C.

Flower description:

*Flowering habit.*—Male flowers, single with one whorl of four tepals. Female flowers, semi-double with three tepals interior to outer whorl of five tepals. Usually about three flowers per cyme. Flowers persistent.

*Natural flowering season.*—Plants will flower continuously, but typically plants flower more abundantly during the spring and summer.

*Flowers.*—Shape: Rounded; somewhat cup-shaped. Diameter: About 2.4 cm. Depth (height): About 1.2 cm. Aspect: Drooping about 60° from vertical. Fragrance: None.

*Flower buds.*—Shape: Ovoid; bulbous with marginal lip. Length: About 11 mm. Diameter: About 8 mm. Color: Close to 145C; towards apex, 55A.

*Tepals.*—Arrangement: Rosette. Length: About 1.6 cm. Width: About 1.1 cm. Shape: Ovate with obtuse apex. Margin: Entire. Texture: Smooth, waxy; iridescent, translucent. Color: Fully opened, upper surface: 55C to 55D with pellucid veins. Fully opened, lower surface: 56A to 56D.

*Peduncles.*—Angle: About 20° from vertical. Length: About 5 cm. Diameter: About 2.5 mm. Strength: Firm. Texture: Smooth, waxy. Color: 144C.

*Pedicels.*—Angle: About 30° from vertical. Length: About 1.7 cm. Diameter: About 1.5 mm. Strength: Moderate. Texture: Smooth, waxy. Color: 50A towards base, 50C towards apex.

*Reproductive organs.*—Male flowers: Stamen quantity: Anther shape: Rhomboidal; lower sides curved inwardly. Anther length: About 2 mm. Filament length: About 1 mm. Pollen: Not observed. Female flowers: Pistil length: About 2.2 cm. Stigma shape: Funnel; bilobate. Stigma color: 163B. Ovary: Inferior; three-winged; one large top wing and two lower wings, both surfaces, 50A.

Disease resistance: Resistance to diseases common to Rex Bogonia has not been determined.

Seed production: Seed production has not been observed.

It is claimed:

1. A new and distinct cultivar of Rex Begonia plant named 'Boston Cherries 'n Chocolate', as illustrated and described.

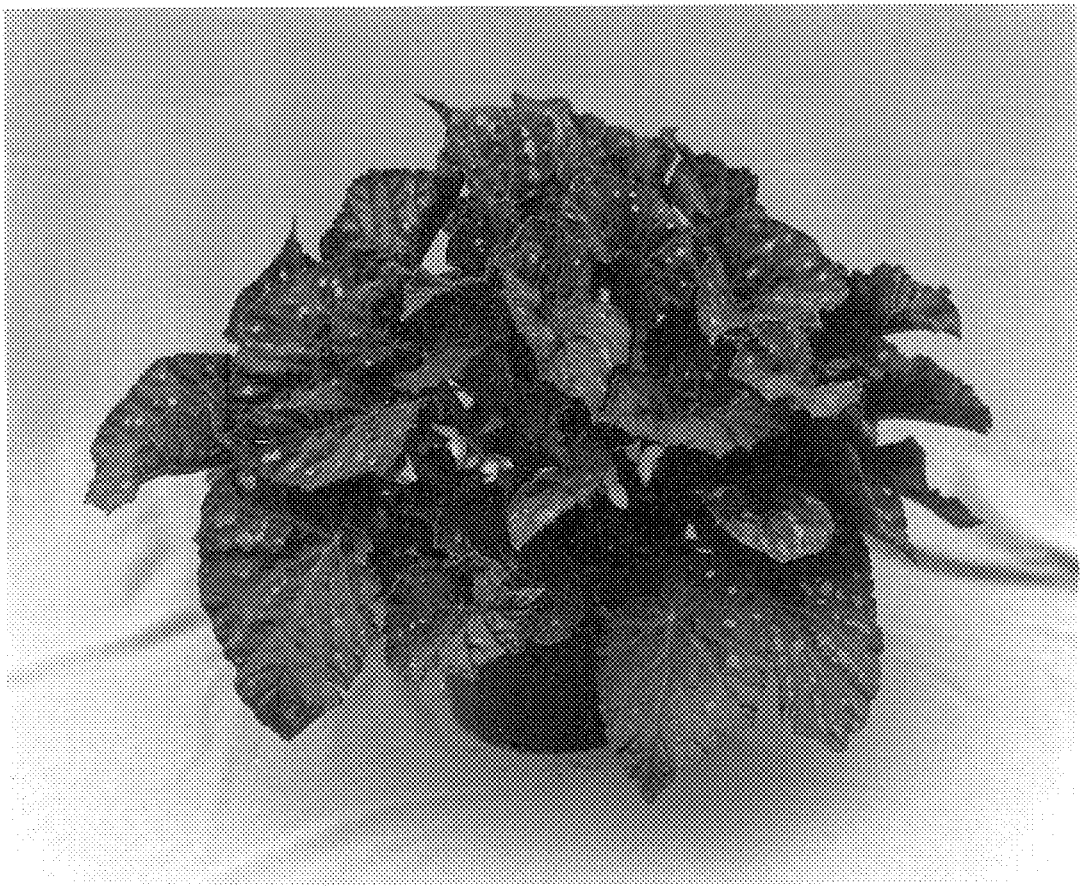

* * * * *